(12) United States Patent
Aruffo et al.

(10) Patent No.: US 6,210,669 B1
(45) Date of Patent: Apr. 3, 2001

(54) METHODS AND COMPOSITIONS FOR IMMUNOMODULATION

(75) Inventors: Alejandro A. Aruffo, Belle Mead, NJ (US); N. Jan Chalupny, Seattle, WA (US); Lieping Chen, Rochester, MN (US); Robert S. Mittler, Flemington, NJ (US); Walter W. Shuford, Redmond; Anthony W. Siadak, Seattle, both of WA (US)

(73) Assignee: Bristol-Myers Squibb Co., New York, NY (US)

( * ) Notice: Subject to any disclaimer, the term of this patent is extended or adjusted under 35 U.S.C. 154(b) by 0 days.

(21) Appl. No.: 08/943,529

(22) Filed: Oct. 3, 1997

Related U.S. Application Data

(60) Provisional application No. 60/028,270, filed on Oct. 11, 1996.

(51) Int. Cl.[7] .................. A61K 39/395; A61K 45/00; C07K 16/28
(52) U.S. Cl. ..................... 424/144.1; 424/154.1; 424/278.1; 530/387.3; 530/388.22; 530/389.1
(58) Field of Search ............. 424/154.1, 144.1, 424/278.1; 530/387.3, 388.22, 389.1

(56) References Cited

U.S. PATENT DOCUMENTS 5,084,391 * 1/1992 Wijdenes et al. ............... 435/240.27

FOREIGN PATENT DOCUMENTS 595659 5/1994 (EP) .
96/29348 9/1996 (WO) .

OTHER PUBLICATIONS

Chalupny et al., "T–Cell Activation Molecule 4–1BB Binds to Extracellular Matrix Proteins," *Proc. Natl. Acad. Sci.* 89:10360–10364 (1992).

Hollenbaugh et al., "The Human T Cell Antigen gp39, a Member of the TNF Gene Family, is a Ligand for the CD40 Receptor: Expression of a Soluble Form of gp39 with B Cell Co–Stimulatory Activity," *EMBO J.* 11(12):4313–4321 (1992).

Pollok et al., "Novel T Cell Antigen 4–1BB Associates with the Protein Tyrosine Kinase p56$^{Tck1}$" *J. Immunol.* 151:1255 (1993).

Goodwin et al., "Molecular Cloning of a Ligand for the Inducible T Cell Gene 4–1BB: A Member of an Emerging Family of Cytokines with Homology to tumor Necrosis Factor," *Eur. J. Immunol.* 23:2631 (1993).

Zhou et al., "Functional Analysis of T–Cell Antigen 4–1BB in Activated Intestinal Intra–epithelial T Lymphocytes," *Immunol. Letters* 41:177–184 (1994).

Alderson et al., "Molecular and Biological Characterization of Human 4–1BB and its Ligand," *Eur. J. Immunol.* 24:2219–2227 (1994).

* cited by examiner

*Primary Examiner*—Christina Y. Chan
*Assistant Examiner*—F. Pierre VanderVegt
(74) *Attorney, Agent, or Firm*—Townsend and Townsend and Crew LLP

(57) ABSTRACT

The instant invention discloses the unexpected result that two anti-4-1BB monoclonal antibodies can inhibit both primary and secondary humoral responses to at least T-cell dependent antigens in vivo. Such antibodies provide a novel approach to immunosuppression and cancer therapy in vivo.

9 Claims, 14 Drawing Sheets

SEQUENCE LISTING

<160> NUMBER OF SEQ ID NOS: 2

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 1
gcggcggatc cccgcaccga gcctcggcca gcg         33

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 2
cgctctagag gatagttctc attcccatgg         30

METHODS AND COMPOSITIONS FOR IMMUNOMODULATION

This application claims the benefit of U.S. Provisional Application No. 60/028,270, filed Oct. 11, 1996, the disclosure of which is incorporated by reference.

BACKGROUND OF THE INVENTION 4-1BB is an inducible T cell receptor that belongs to the nerve growth factor receptor superfamily. This novel antigen is expressed on the surface of activated splenic T cells and thymocytes. The extracellular domain of this type I transmembrane protein is homologous to members of the nerve growth factor receptor superfamily. The cytoplasmic domain contains a sequence homologous to the binding site for T-cell-specific tyrosine kinase $p56^{1ck}$.

The in vivo role of 4-1BB remains unclear, although increasing evidence indicates involvement as a signaling molecule in T cell activation. For example, cross-linking of 4-1BB with monoclonal antibody 53A2 on anti-CD3-stimulated T cells results in a 2 to 10-fold enhancement of T cell proliferation (Pollok et al. *J. Immunol.* 151:1255 (1993)). Furthermore, Zhou et al. (*Immunol. Letters* 41:177–184 (1994)) have demonstrated that 4-1BB is expressed on activated intestinal intra-epithelial T lymphocytes (IELS), and that activated IELS triggered with anti-4-1BB monoclonal antibody could enhance the level of IEL cytotoxicity against anti-CD4-secreting hybridoma cells. Cross-linking of anti-4-1BB antibody also enhanced proliferation of IELS.

At least two candidate ligands of 4-1BB have been identified. Chalupny et al. (*Proc. Natl. Acad. Sci. U.S.A.* 89:10360–10364 (1992)) used a soluble 4-1BB immunoglobulin fusion protein (4-1BB Rg) to demonstrate that 4-1BB binds to extracellular matrix protein (EMC). Goodwin et al. (*Eur. J. Immunol.* 23:2631 (1993)) reported the isolation of a cDNA for a ligand for murine 4-1BB (4-1-BB-L) that is a member of an emerging family of ligands with C-terminal amino acid homology which includes TNF, lymphotoxin (LT)-alpha and beta, CD40-L, CD27-L, CD30-L, and Fas-L. The human analog (hu4-1BB) of murine 4-1BB and a human analog (hu4-1-BB-L) of murine 4-1-BB-L have been cloned (Alderson et al. *Eur. J. Immunol.* 24:2219–2227 (1994)). Both monoclonal antibody to hu4-1BB and cells transfected with hu4-1-BB-L induced a strong proliferative response in mitogen co-stimulated primary T cells.

Thus, a need exists for the development of antagonists of 4-1BB. The instant invention addresses this need and more.

SUMMARY OF THE INVENTION

One aspect of the invention is a method for suppressing a primary and secondary humoral response to an antigen in a host comprising administering to the host an effective dose of an anti-4-1BB antibody.

Further aspects of the invention are compositions comprising monoclonal antibodies 1D8, 3B8, or 3E1.

A further aspect of the invention is a composition comprising an anti-4-1BB antibody, wherein the antibody inhibits an antibody response to sheep red blood cells in vivo.

Another aspect of the invention is a method for blocking T cell dependent immune responses in a host comprising administering to the host an effective dose of an anti-4-1BB antibody.

Another aspect of the invention is a method for enhancing lymphocytic killing of tumor cells in a host comprising administering to the host an effective dose of an anti-4-1BB antibody.

Another aspect of the invention is a method for potentiation of development of cytotoxic T cells in a host comprising administering to the host an effective dose of an anti-4-1BB antibody.

Another aspect of the invention is a method for treating a host having a T cell autoimmune disease comprising administering to the host an effective dose of an anti-4-1BB antibody.

DESCRIPTION OF THE SPECIFIC EMBODIMENTS

Figure 1:
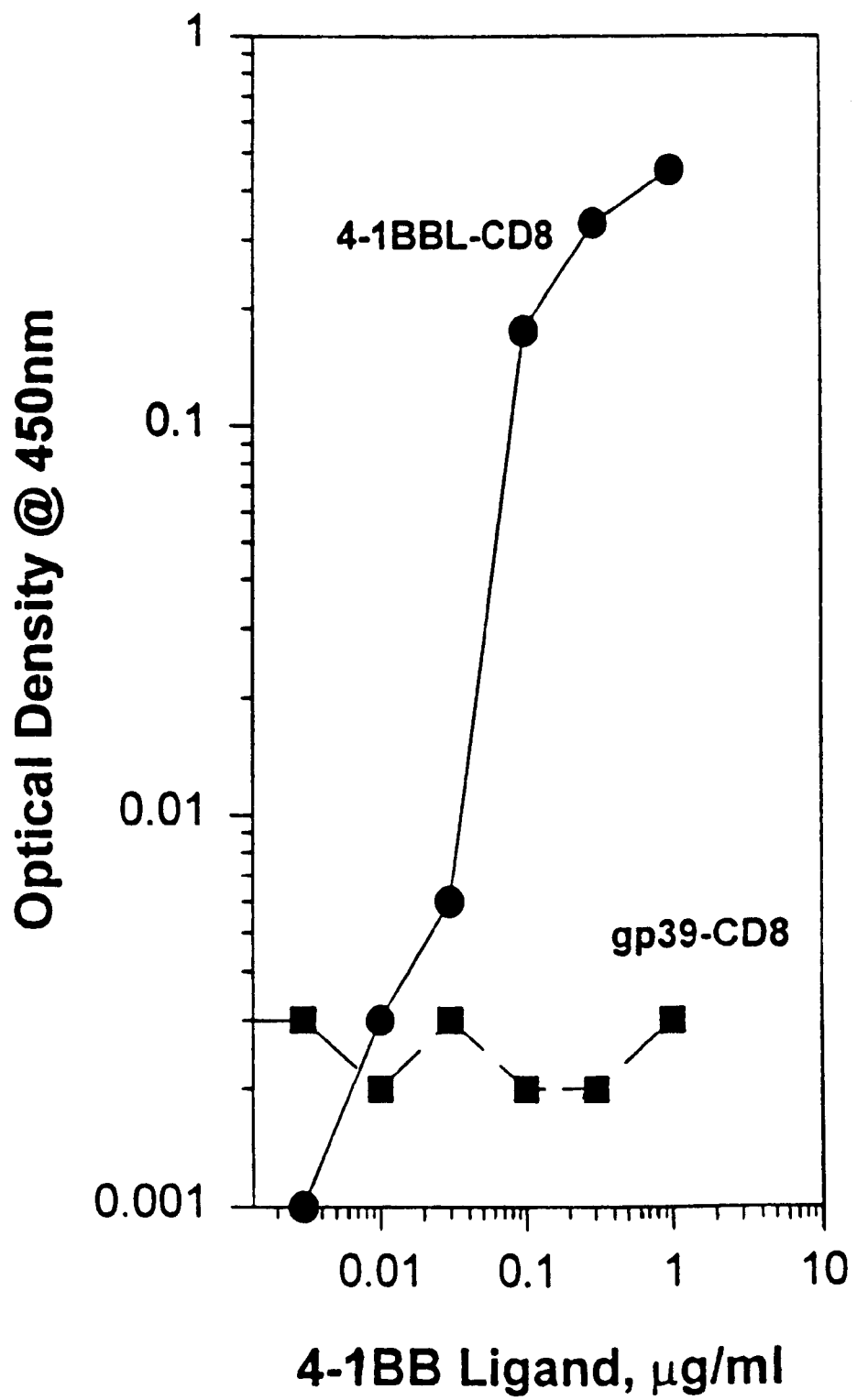
FIG. 1 is a graph depicting the binding of murine 4-1BB ligand to immobilized 4-1BB.

Immunosuppressive therapies are commonly used in the control of inflammation, treatment of cancer, and transplantation of organs. Traditional therapies, such as the use of adrenocortical hormones and their inducer, adrenocorticotropic hormone, chemotherapeutic agents, and radiation therapy can result in non-specific immunosuppression and immunodeficiencies. Thus, a substantial need exists for alternate routes of inducing immunosuppression. The antibodies of the instant invention provide an opportunity to preferentially target particular polypeptides, i.e., 4-1BB, expressed on T cells.

The term "4-1BB" as used herein is intended to refer to the murine cell surface protein 4-1BB and to homologues of this protein present in other species, including humans. Although some amino acid sequence homology is expected between homologues in different species, the degree of homology can be as low as about 50%. Thus, homologues of 4-1BB are defined as being transmembrane proteins expressed on activated T cells having at least 50% amino acid sequence homology to murine 4-1BB. Furthermore, alleles of 4-1BB and homologues, 4-1BB and homologues with conservative amino acid substitutions, and soluble forms of 4-1BB and homologues are included in this definition of 4-1BB.

The term "humoral response" as used herein is intended to refer to an immune reaction that can be transferred with serum, typically resulting from the presence of specific antibody. The terms "primary" and "secondary" immune responses refer to the host's first exposure to antigen and subsequent exposures to antigen, respectively. Typically, in the humoral immune response, the major class of antibody during the early primary response (i.e., the first week) is IgM, while IgG is the major class of antibody in the secondary response.

The monoclonal antibodies of the instant invention can be of any class, but preferably are IgG or IgM.

For administration to humans, e.g., as a component of a composition for in vivo treatment, the monoclonal antibodies of the invention are preferably substantially human to minimize immunogenicity, and are in substantially pure form. By "substantially human" is meant that the immunoglobulin portion of the composition generally contains at least about 70% human antibody sequence, preferably at least about 80% human, and most preferably at least about 90–95% or more of a human antibody sequence. When referring to "antibody," it will be understood that non-immunoglobulin sequences may optionally be present in the molecule so long as the molecule retains the ability to bind 4-1BB.

It may be desirable to transfer antigen binding regions (e.g. the F(ab')$_2$, variable or hypervariable (complementarity determining) regions), of non-human monoclonal antibodies, such as from a murine monoclonal antibody that has been made to the human 4-1BB homologue, to human constant regions (Fc) or framework regions using recombinant DNA techniques, thereby producing substantially human molecules. Such methods are generally known in the art and are described in, for example, U.S. Pat. No. 4,816,397, EP publications 173,494 and 239,400, which are incorporated herein by reference. Alternatively, one may isolate DNA sequences which encode a human monoclonal antibody or portion thereof that specifically binds to 4-1BB by screening a DNA library from human B cells according to the general protocol outlined by Huse et al., *Science* 246:1275–1281 (1989), and described in WO 90/14430, incorporated herein by reference, and then cloning and amplifying the sequences which encode the antibody (or binding fragment) of the desired specificity. In yet other embodiments, single chain binding polypeptides can be made which bind to 4-1BB. These single chain polypeptides may be produced by cloning and joining the variable regions of the heavy and light chains of a monoclonal antibody which binds to 4-1BB. Methods for the production of single chain binding polypeptides are described in detail in, e.g., U.S. Pat. No. 4,946,778, which is incorporated herein by reference.

As used herein, the terms "treatment" or "treating" include: (1) preventing undesirable symptoms or pathological states from occurring in a subject who may be predisposed to these undesirable symptoms or pathological states but who has not yet been diagnosed as having them; (2) inhibiting undesirable symptoms or pathological states, i.e., arresting their development; or (3) ameliorating or relieving undesirable symptoms or pathological states, i.e., causing regression of the undesirable symptoms or pathological states. An amount of the compositions of the invention which accomplishes any of these goals is termed an "effective amount", and intended to include both prophylactic and therapeutic uses of the compositions.

The antibodies of the invention are useful in the prevention or treatment of diseases or pathological states benefiting from immunosuppressive therapies, including but not limited to inflammatory bowel disease, multiple sclerosis, autoimmune diabetes, rheumatoid arthritis, graft vs. host disease, systemic lupus erythematosus, other T cell autoimmune diseases, and cancer.

The monoclonal antibodies or other compounds useful in the present invention can be incorporated as components of pharmaceutical compositions containing a therapeutic or prophylactic amount of at least one of the monoclonal antibodies or binding fragment thereof with a pharmaceutically effective carrier.

In preparing the pharmaceutical compositions useful in the present methods, a pharmaceutical carrier should be employed which is any compatible, nontoxic substance suitable to deliver the antibodies or binding fragments thereof or therapeutic compounds identified in accordance with the methods disclosed herein to the patient. Sterile water, alcohol, fats, waxes, inert solids and even liposomes may be used as the carrier. Pharmaceutically acceptable adjuvants (buffering agents, dispersing agents) may also be incorporated into the pharmaceutical composition. The antibodies and pharmaceutical compositions thereof are particularly useful for parenteral administration, i.e., intravenously, intraarterially, intramuscularly, or subcutaneously. However, intranasal or other aerosol formulations are also useful. The concentration of compound such as an antibody in a formulation for administration can vary widely, i.e., from less than about 0.5%, usually at least 1% to as much as 15 or 20% or more by weight, and will be selected primarily based on fluid volumes, viscosities, etc., preferred for the particular mode of administration selected. Actual methods for preparing administrable compositions will be known or apparent to those skilled in the art and are described in more detail in, for example, *Remington's Pharmaceutical Science*, 17th Ed., Mack Publishing Co., Easton, Pa. (1985), which is incorporated herein by reference.

The compounds of the invention useful in inhibiting the immune response to an antigen or antigens can be administered for prophylactic or therapeutic treatment. In treatments intended for prophylactic applications, the compositions are administered to a patient likely to be exposed to a particular antigen or antigens, such as in patients receiving tissue transplants (including transfusions of blood or serum) or immunogenic compounds such as antibiotics. Administration of the compounds of the invention can be done prior to exposure to the antigen or antigens or at the same time. To prevent recurrent disease and the sequelae thereof, the compositions may be administered daily, weekly or other scheduled maintenance therapy. The regimen will also depend on the dosage and effectiveness thereof, the intended use and the patient's general state of health. The treating physician, dentist, or other health professional will select dose levels and pattern of administration, i.e., route and single or multiple administrations.

In therapeutic applications, the compounds of the invention are administered to a patient already suffering from undesirable symptoms or pathology in an amount sufficient to at least partially suppress the immune response to the antigen(s). An amount adequate to accomplish this is defined as a "therapeutically effective dose." Amounts effective for this use will depend upon the compound being employed, the route of administration, the severity of the undesirable symptoms or pathological states and the general state of the patient's health. Determination of an effective amount of a compound of the invention to suppress the immune response to an antigen can be determined by techniques well known in the art. For example, a decrease in antigen-specific immunoglobulin and thus efficacy of the subject compositions, can be monitored with a variety of well known in vitro diagnostic procedures.

The antigen (or antigens) to which the host patient is exposed is preferably T-cell dependent. Most antigens are T-cell dependent, i.e., requiring T cells in order to provoke an immunological response. T-independent antigens are typically large polymeric molecules with multiple, repeating antigenic determinants. Frequently, T-independent antigens have mitogenic properties.

In further embodiments of the invention, the anti-4-1BB antibodies of the invention can be used in affinity chromatography to purify 4-1BB polypeptides, such as the extracellular region of 4-1BB, soluble forms of 4-1BB, and fusions of 4-1BB to other molecules such as immunoglobulins. The anti-4-1BB antibodies of the invention can also be labeled with a reporter molecule such as fluorescein, alkaline phosphatase, and the like, and used to visualize the presence of 4-1BB on cell surfaces. Radiolabeled antibodies can be used to quantitate the amount of 4-1BB on cells. In other embodiments, the anti-4-1BB antibodies of the instant invention can be used in competitive assays with ligands of 4-1BB.

The following examples are offered by way of illustration, not by way of limitation.

EXAMPLES

I. Immunization and Screening Protocols

For immunization and screening a fusion protein consisting of the extracellular portion of the murine 4-1BB molecule and human immunoglobulin (Ig) constant region was constructed (EP 0 595 659, hereby incorporated by reference in its entirety). The 4-1BBIg fusion protein contained a site for cleavage by the protease thrombin between the 4-1BB and Ig portions of the molecule. For immunization the fusion protein was cleaved with thrombin, then passed over a protein A column to remove undigested protein and Ig fragments. The unbound material resulting from this procedure, which contained several bands by SDS-PAGE analysis, was used for immunization.

Using immune spleen cells and the mouse myeloma AG8 (Kearney et al. *J. Immunol.* 123:1548–1550 (1974)) cell line as fusion partner, rat-mouse hybridomas were generated and selected using standard techniques. Antibodies were obtained from two separate fusions. The mAbs 3B8 and 1D8 were produced from a fusion following two footpad injections of 20 µg protein in RIBI adjuvant (RIBI Immunochemical) to Sprague-Dawley rats on days 0 and 3; on day 10 the rats received a third footpad injection of 20 µg protein in PBS, and on day 13 the draining popliteal lymph node was removed and a fusion performed. The remaining mAbs were produced in a second fusion of spleen cells following 4 intraperitoneal injections of 20µg protein in RIBI over a 5 month period. An intravenous injection of 30 µg was done 17 and 3 days prior to the fusion.

II. Characterization of the Anti-4-1BB Antibodies

Antibodies were first identified by specific binding to the 4-1BBIg fusion in a standard ELISA. The specificity of the antibodies was established by additional criteria: (1) binding to COS cells expressing the full length 4-1BB molecule but not mock transfected control COS cells; (2) binding to the DO-11-10 T cell hybridoma line that was activated to express 4-1BB (activation for 12 hours with 10 ng/ml PMA, and ionomycin, 0.5 µg/ml). The isotype of 3B8 antibody is rat IgM whereas the other antibodies are all of the IgG2a isotype as determined by using isotype specific peroxidase reagents (Zymed) in an ELISA with the 4-1BBIg protein.

III. Purification of Antibodies

The 3B8 mAb (IgM) was affinity purified on an anti-kappa chain (mAb RG7 (ATCC T1B 172)) column. The mAb was eluted with Immunopure Ig Elution Buffer (Pierce) and then dialyzed against phosphate buffered saline (PBS). The RG7-purified material did contain some free light chains which copurified with the intact antibody. All other antibodies were purified on protein G (Gammabind Plus, Pharmacia). Immunopure Ig Elution Buffer was used to elute the antibody. The eluted antibody was dialyzed against PBS prior to use.

IV. Inhibition of the Binding of 4-1BB Ligand to 4-1BB Protein by mAbs

A soluble fusion protein consisting of the extracellular portion of the 4-1BB ligand at the carboxy terminus and the extracellular portion of murine CD8 at the amino terminus was used as a surrogate to study inhibition of ligand binding to the 4-1BB molecule. DNA encoding the extracellular domain of murine 4-1BB ligand (residues 104–309) was generated by polymerase chain reaction (PCR) using an upstream primer containing a BamHI site (SEQ ID No: 1) (5'-GCGGCGGATCCCCGCACCGAGCCTCGGCCAGCG-3') and a downstream primer containing an XbaI site (SEQ ID No: 2) (5'-CGCTCTAGAGGATAGTTCTCATTCCCATGG-3'). The murine 4-1BB ligand DNA fragment was cloned in frame into the CDM7(B−) vector containing the extracellular domain of CD8 followed by a BamHI site. This molecule will be referred to herein as the 4-1BB ligand (4-1-BBL). The ability of the anti-4-1BB mAbs to block ligand binding to the 4-1BB molecule was evaluated in ELISA and cell-based assay systems. The 4-1-BBL was purified on an anti-CD8 affinity column using mAb 53.6 (ATCC TIB 105) by elution with 40% propylene glycol/60% 50 mM Tris (pH 7.0)/ 1.25 M $(NH_4)_2SO_4$, and dialyzed against phosphate-buffered saline (PBS). The purified material migrated as a predominant broad band of estimated molecular weight of 55,000 in reducing SDS-PAGE. When evaluated by HPLC gel filtration it eluted as 3 peaks. The predominant peak had an estimated molecular weight of 300,000.

Figure 2:
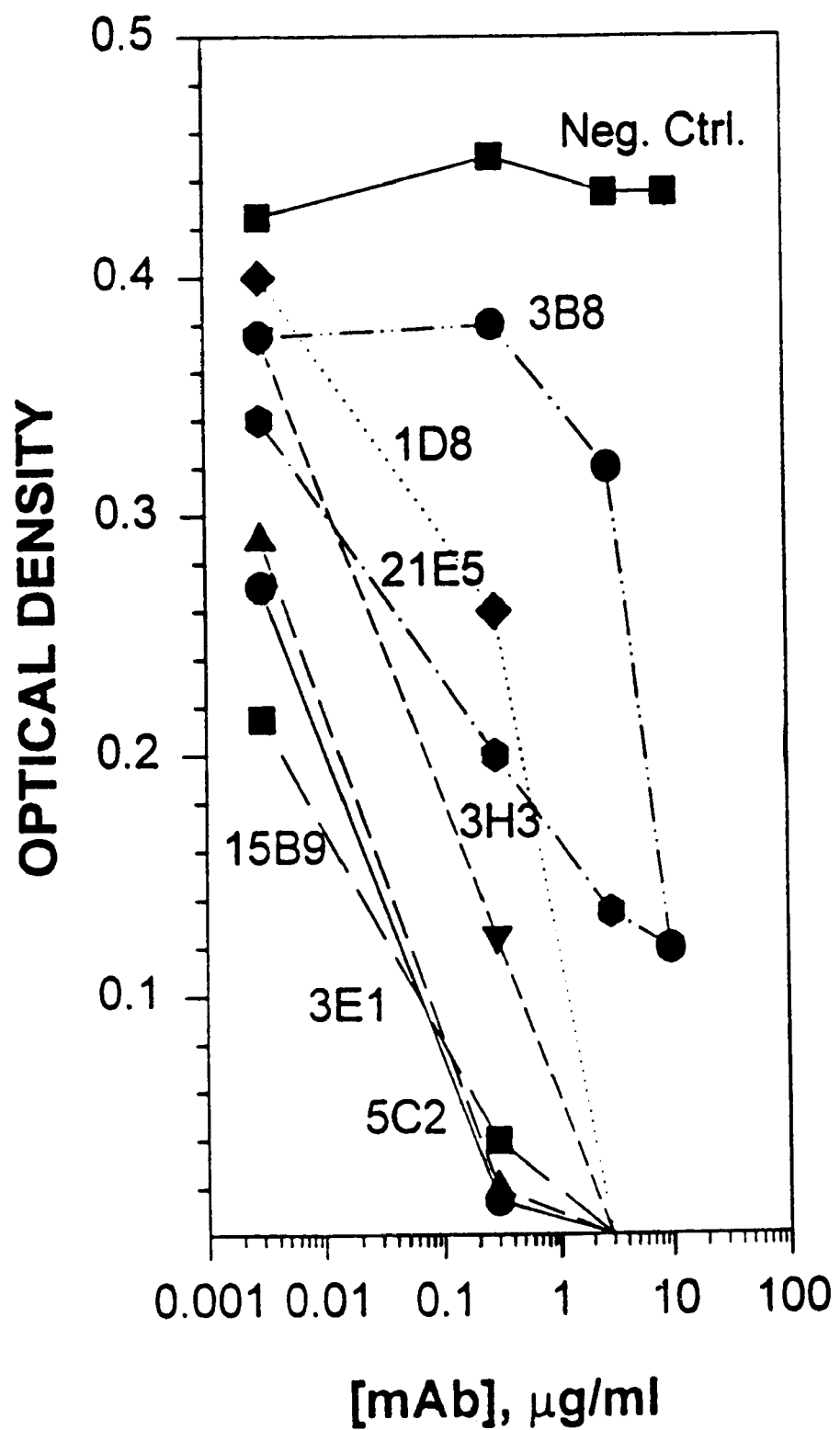
FIG. 2 is a graph depicting the blocking of 4-1BB binding to its ligand by anti-4-1BB monoclonal antibodies (mAb).

The ELISA assay for inhibition of 4-1BBL binding was performed as described below. The 4-1BBIg protein was coated onto ELISA wells at 0.1 µg/ml in PBS overnight at 4° C., blocked with specimen diluent (Genetic Systems), and incubated with purified antibody for 1 hour. Ligand was then added and the mixture of mabs and ligand was incubated for one additional hour. The plates were washed and incubated with biotinylated mAb 53.6 (anti-CD8), followed by streptavidin-horse radish peroxidase (HRPO) conjugate. Inhibition of binding was indicated by a drop in ELISA signal. A titration of ligand binding to 4-1BBIg is shown in FIG. 1. The murine gp39-CD8 fusion protein control did not bind 4-1BB, whereas the 4-1BB ligand specifically bound to 4-1BB in a dose-dependent fashion. The ability of the mAbs to block binding of the ligand to 4-1BBIg in a similarly formatted ELISA is shown in FIG. 2.

V. Activation of DO-11-10 Cells to Express 4-1BB Protein

Figure 3:
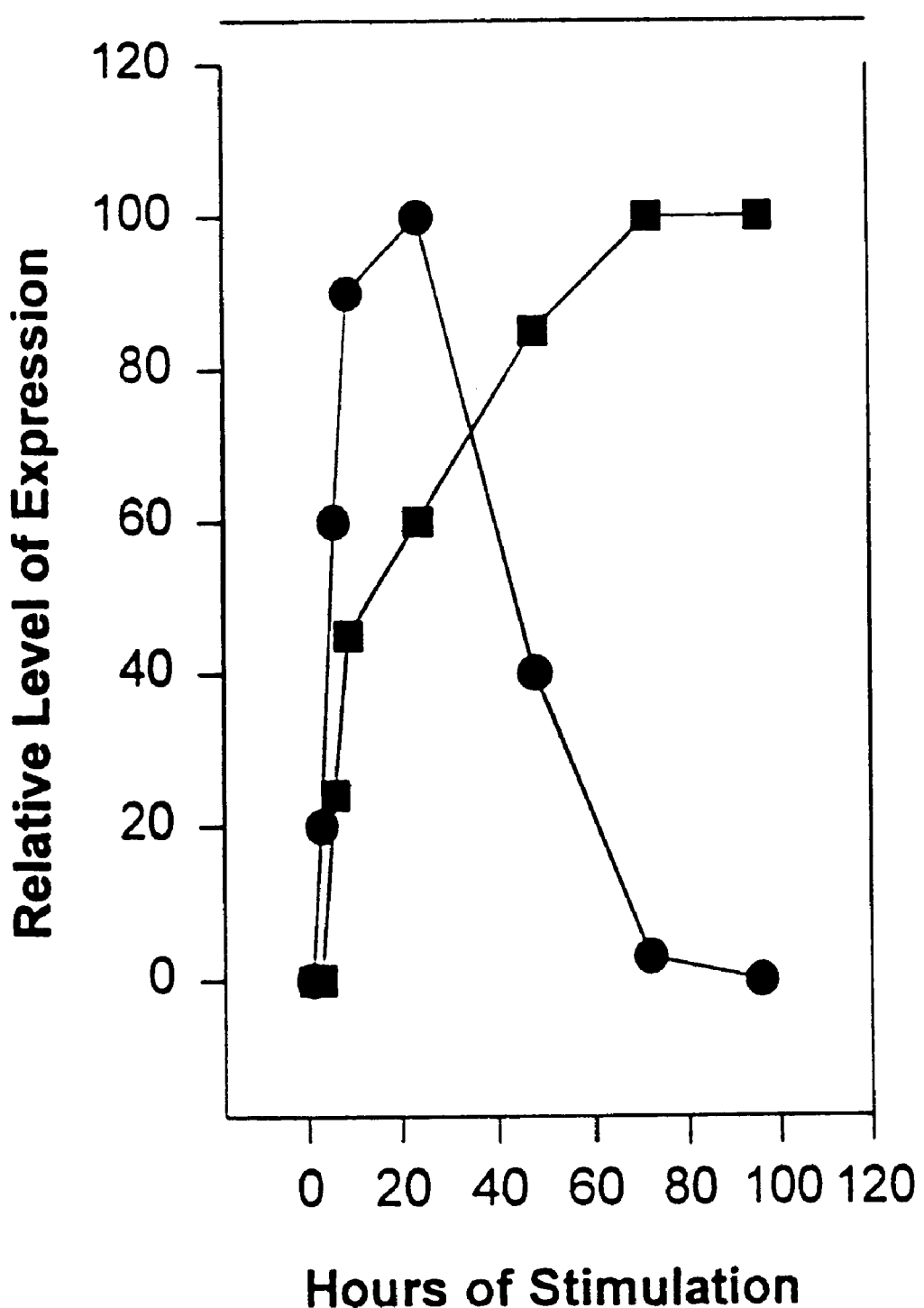
FIG. 3 is a graph depicting the expression of 4-1BB in activated T cells as a function of time after stimulation. The circles represent 4-1BB mRNA levels. The squares represent levels of 4-1BB receptor on the surface of activated T cell line DO-11-10.

The T cell hybridoma DO-11-10 was activated to express the 4-1BB molecule by treatment with PMA (10 ng/ml) and ionomycin (0.5 µg/ml) for varying amounts of time, after which 4-1BB mRNA or cell surface expression of the 4-1BB was measured by Northern analysis or FACS analysis, respectively (FIG. 3). Untreated cells failed to bind the 4-1BBL protein. Activated cells bound the 4-1BBL protein but not a similar fusion protein construct of gp39 and Lyt 2a (Hollenbaugh et al. *EMBO J.* 11(12):4313–4321 (1992)). The anti-4-1BB antibodies 1D8 and 3B8 bound to DO-11-10 cells only when the cell line was activated. Preincubation of those mAbs with DO-11-10 cells could block the subsequent binding of 4-1BBL. The binding of 4-1BBL to cells was determined using anti-CD8 mAb (53.6) conjugated antisera (Biosource).

Figure 4:
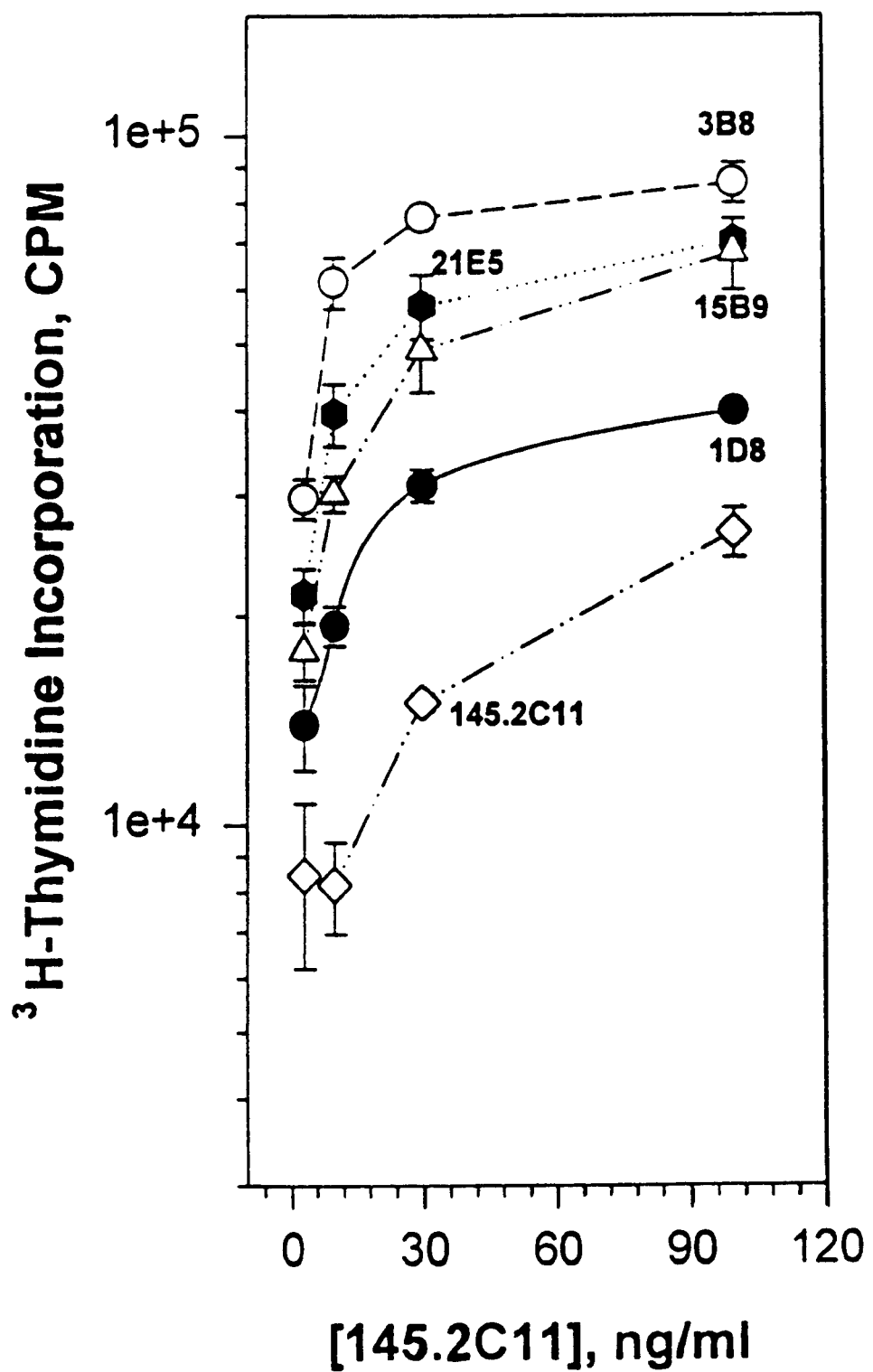
FIG. 4 is a graph depicting costimulation of T cell activation by suboptimal doses of anti-CD3 monoclonal antibody 145.2C11 and anti-4-1BB monoclonal antibodies.

In further experiments, the ability of the anti-4-1BB antibodies to costimulate T cell activation was investigated. Stimulation of resting T cells with suboptimal doses of anti-CD3 mAb 145.2C11 and 10 µg/ml anti-4-1BB mAbs enhanced proliferation 2.5-8 fold over 145.2C11 alone (FIG. 4). There was little correlation between binding affinity or ability to block ligand binding and the ability of the mAbs to costimulate T cells.

VI. Inhibition of Development of Anti-SRBC Antibody Response by the Anti-4-1BB Monoclonals 1D8 and 3B8

Figure 5:
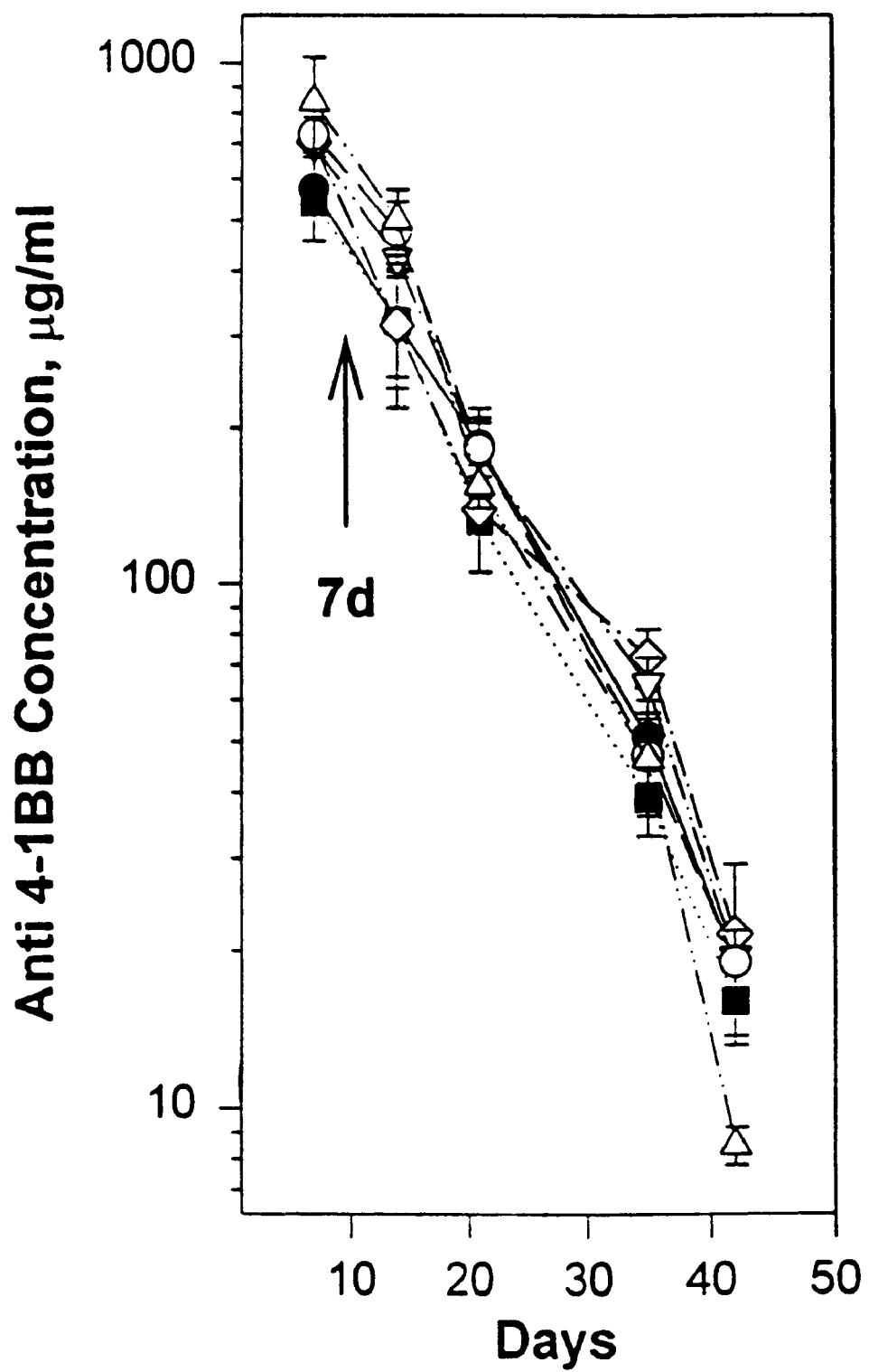
FIG. 5 is a graph depicting the pharmacokinetics of anti-4-1BB monoclonal antibody 1D8. Each symbol represents a different mouse.

The pharmacokinetics of anti-4-1BB mAb 1D8 were assessed following i.v. injection of 250 mg/mouse. Serum samples were collected beginning on day 8 and ending on day 42 and were analyzed for anti-4-1BB mAb. The results, shown in FIG. 5, demonstrated that the half life of 1D8 was 7 days. These results also demonstrated that an anti-ratIgG (anti-1D8) was not generated in these animals. The half-life of 3B8, a rat IgM antibody, was 6.5 hr (data not shown).

Figure 6:
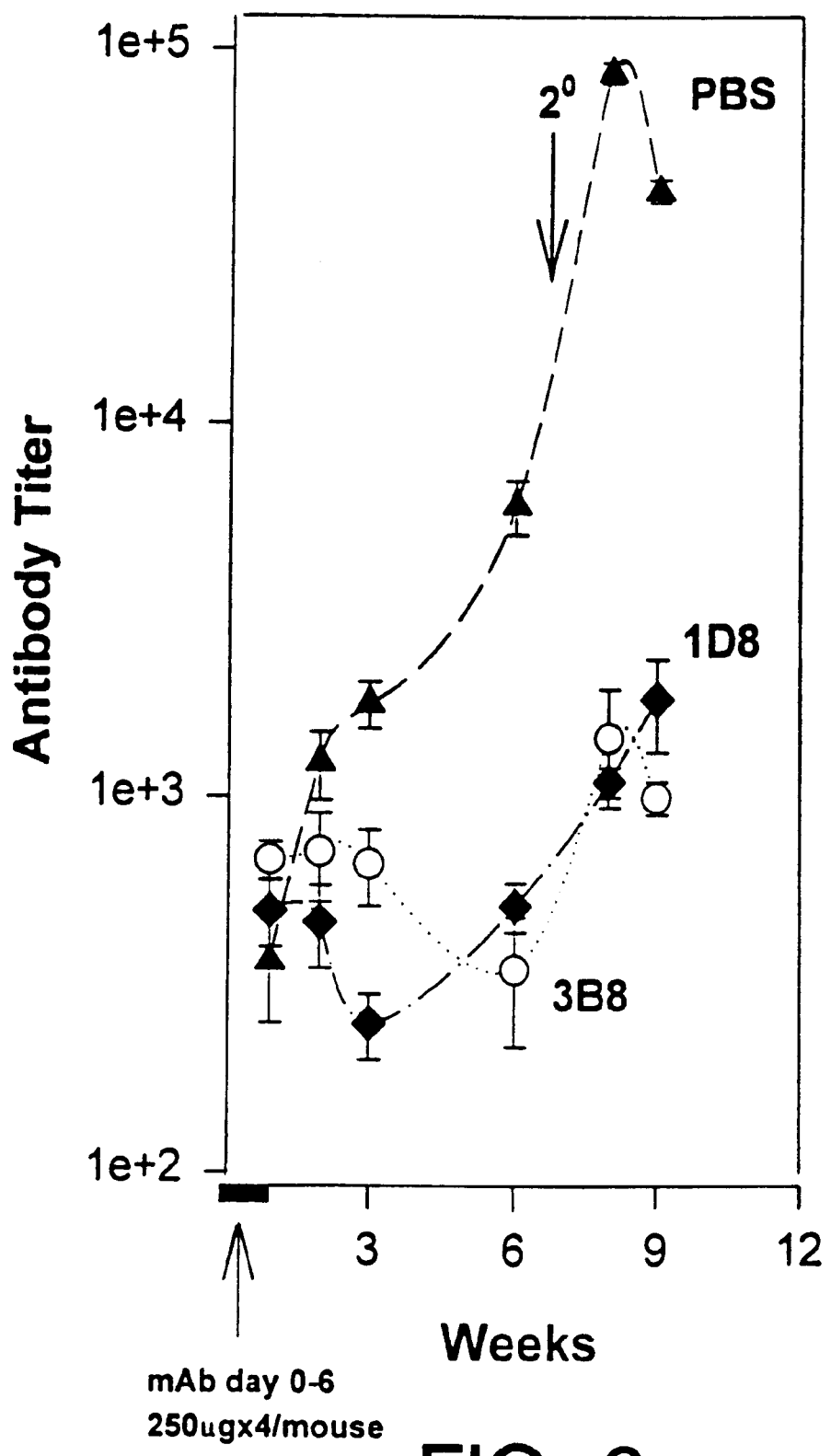
FIG. 6 is a graph depicting the inhibition of primary and secondary anti-sheep red blood cell response by anti-4-1BB antibodies.

Groups of five mice were injected i.v. with the T cell dependent antigen sheep red blood cell (SRBC) and 250 mg of either 1D8 or 3B8. Further injections of antibody were administered every second day through day 6. Serum samples were taken from each mouse periodically up to week 7 and assayed for anti-SRBC titer. On week 7 the mice received a secondary challenge of SRBC but no further administration of anti-4-1BB mAb. Serum samples were collected over a two week period and measured for anti-SRBC antibodies. Both 1D8 and 3B8 blocked both primary and secondary challenge to SRBC (FIG. 6). These experiments, particularly the results with 3B8, indicate that this treatment leads to long term non-responsiveness.

VII. Inhibition of Generation of Cytoxic T Cells

Figure 7:
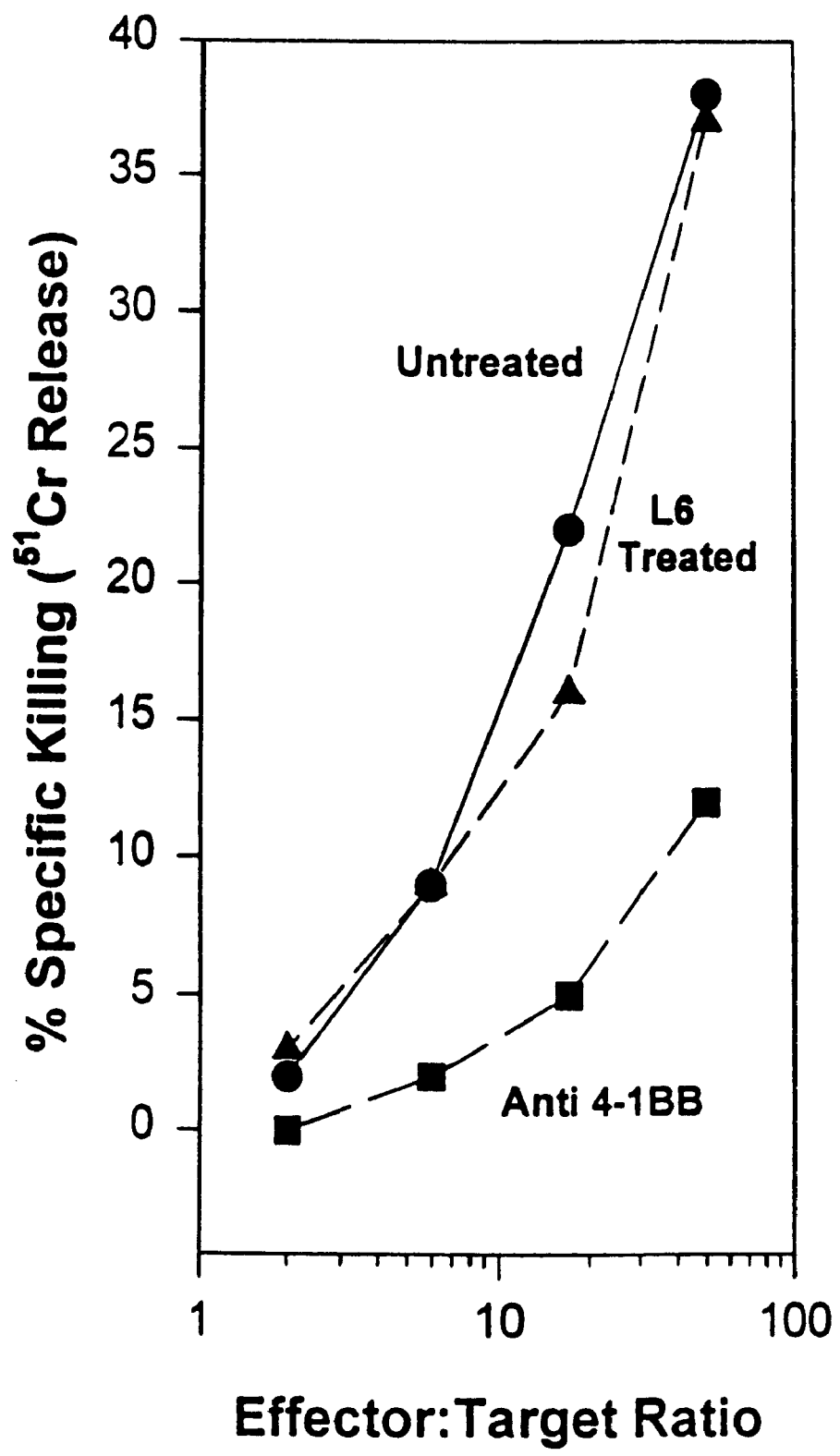
FIG. 7 is a graph depicting the inhibition of cytotoxic T cell generation by anti-4-1BB antibodies.

In order to determine if 4-1BB expression is important for other T cell effector functions, the abilities of 1D8 mAb and several mAbs derived from the second fusion to affect the generation of CTL during acute graft versus host disease (GvHD) were measured. Splenic T cells were isolated from $BDF_1$ ($H-2^{db}$) mice 10 days after i.v. injection of $10^7$ C57BL/6($H-2^b$) splenic T cells. Following 5 days of expansion in tissue culture with recombinant mouse IL-2(R&D Systems) at 2-10ng/ml, viable T cells were assayed for cytotoxicity against either $Ia^d$ (P815) or $Ia^b$ (EL4) $^{51}$Cr-labelled targets. The results in FIG. 7 show that splenic T cells treated with a control mAb or PBS effectively kill targets bearing the appropriate MHC class II haplotype ($Ia^d$) at ratios as low as 3:1. In contrast, splenic T cells from mice injected with 1D8 were not able to kill until the E:T ratio reached 50:1, and even there killing was reduced by 75%. Similar results were obtained with mAb 22B6. While mAb 3E1 was completely inhibitory, mAb 21E5 was less effective at inhibiting the generation/survival of CTL. No killing was observed on EL-4($Ia^b$) targets (data not shown). These observations could not be accounted for by the presence of anti-4-1BB mAb in the cultures since addition of such antibodies to the CTL assays did not block CTL killing. Microscopic examination of the cultured T cells prior to adding them to targets revealed a complete lack of activated cells, many small resting viable cells and a substantial number of apoptotic or dead cells that were absent from the control cultures.

VIII. Enhancement of CTL Generation During In Vivo GvHD

From the studies described above, GvHD mice treated with anti-4-1BB mAbs failed to demonstrate CTL activity against an appropriate target following 5 days of in vitro culture with IL-2 or without IL-2 (data not shown) whereas control mice developed prominent CTL responses in the presence of IL-2. This observation was surprising since remarkable 1D8-induced CTL killing of tumor cells was consistently discovered in separate in vivo tumor models of both metastatic and non-metastatic disease (FIGS. 8, 9, 10 and 11). In addition, spleens removed from anti-4-1BB treated GvHD mice were enlarged 2–3 times the size of normal spleens as were the Ab control mice. To address this paradoxical observation, the GvHD experiments were repeated as before but this time CTL activity was assessed immediately following the surgical removal of the spleen, eliminating in vitro IL-2 expansion of CTL. The results of this experiment are markedly different from the results reported above. In FIG. 12A, it can be seen that two anti-4-1BB mabs, 1D8 and 22B6, each known to bind to a different region of the 4-1BB molecule enhanced CTL activity by nearly fourfold over that observed in control GvHD animals. In contrast, mAb 21E5 had no apparent effect upon CTL generation while mAb 3E1, one of the most potent blockers of ligand binding, completely inhibited CTL development. The powerful effect of both 1D8 and 22B6 mAbs on the enhanced development of CTL activity is further demonstrated in FIG. 12B which shows the marked reduction in the number of total viable splenocytes retrieved from mice treated with these two antibodies. In addition, phenotypic analysis of splenocytes revealed that the percentage of $CD8^+$ T cells increased to 30% of the total cell number in mice treated with the 1D8 mAb (FIG. 12C) whereas GvHD mice injected with 6E9, the isotyped matched non-binding control or those receiving no antibody had 5% to 8% $CD8^+$ T cells. Epitope mapping studies of anti-4-1BB mAbs using 4-1BB fusion proteins in which domain swapping was carried out demonstrated that the 1D8 mAb was unique in that it bound to the membrane proximal region of the extracellular domain of the 4-1BB molecule not involved in 4-1BBL binding (data not shown).

IX. Potentiation of Development of Cytotoxic T Cells

In these experiments anti-4-1BB monoclonal antibodies were used to potentiate the development of cytotoxic T cells which then kill both weakly and non-immunogenic tumors that are highly metastatic.

Figure 8:
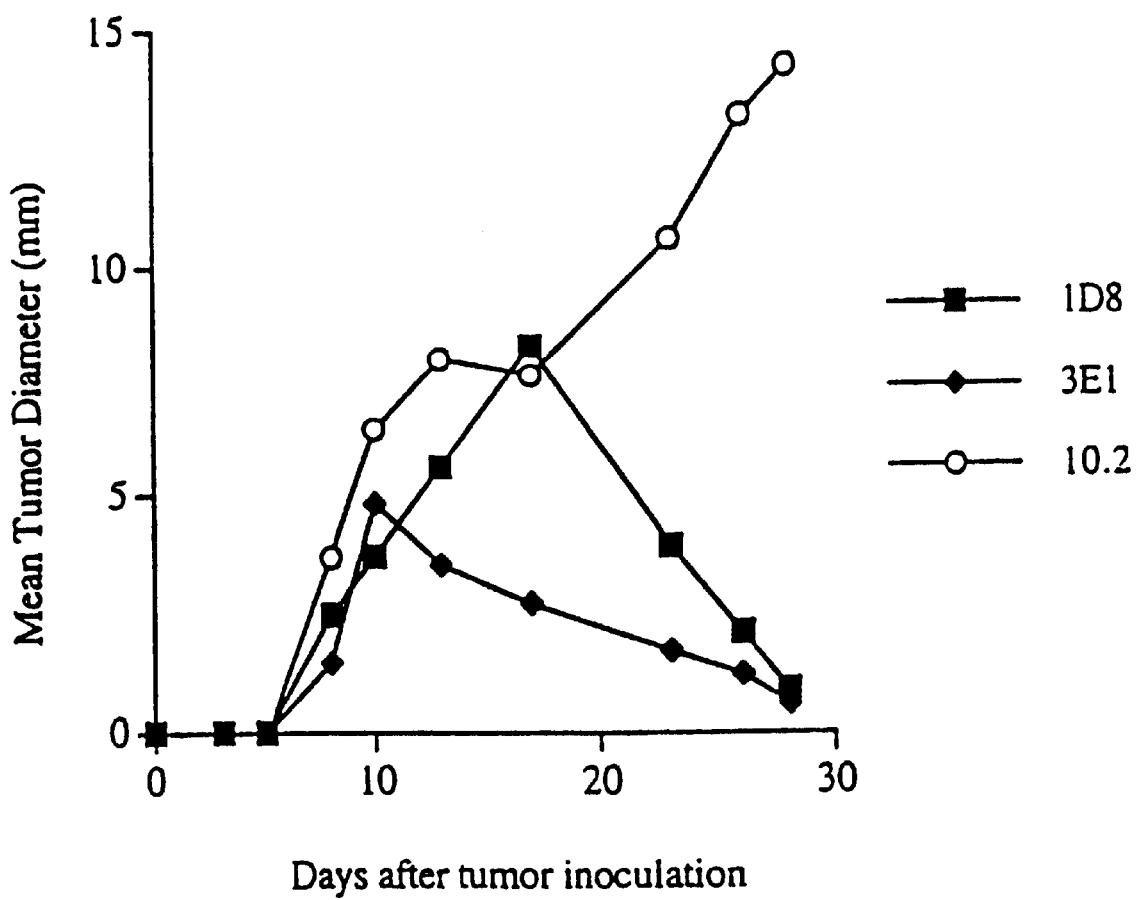
FIG. 8 is a graph depicting regression of P815 tumor following treatment with mAb to 4-1BB.

FIG. 8 depicts results from an experiment in which groups of five Balb/C mice were injected subcutaneously with $10^5$ P815 mastocytoma cells on day 0. Control mice received the anti-human CD5 mAb 10.2. However, mice injected with either 1D8 or 3E1 (anti-4-1BB) mAbs rapidly rejected their tumors. Antibody injections were given on days 3 and 6, 400mg/mouse intraperitoneally.

Figure 9:
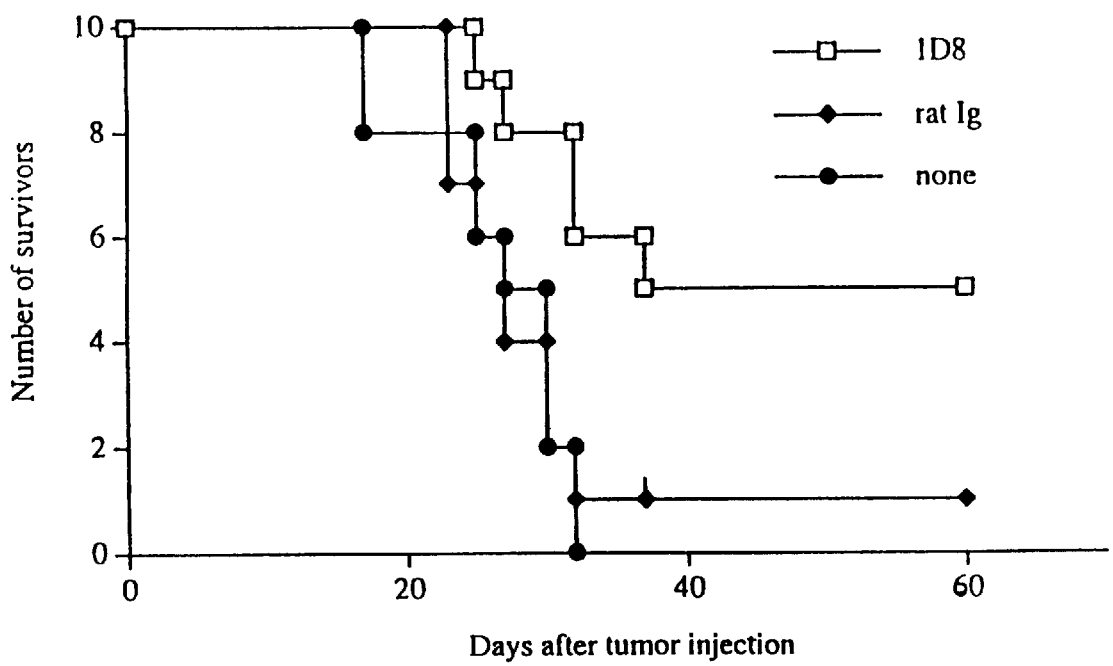
FIG. 9 is a graph depicting long-term survival of mice bearing P815 ascites following treatment with anti-4-1BB mAb.

FIG. 9 depicts the long term survival of mice given the P815 tumor and treated with the 1D8 mAb.

Figure 10:
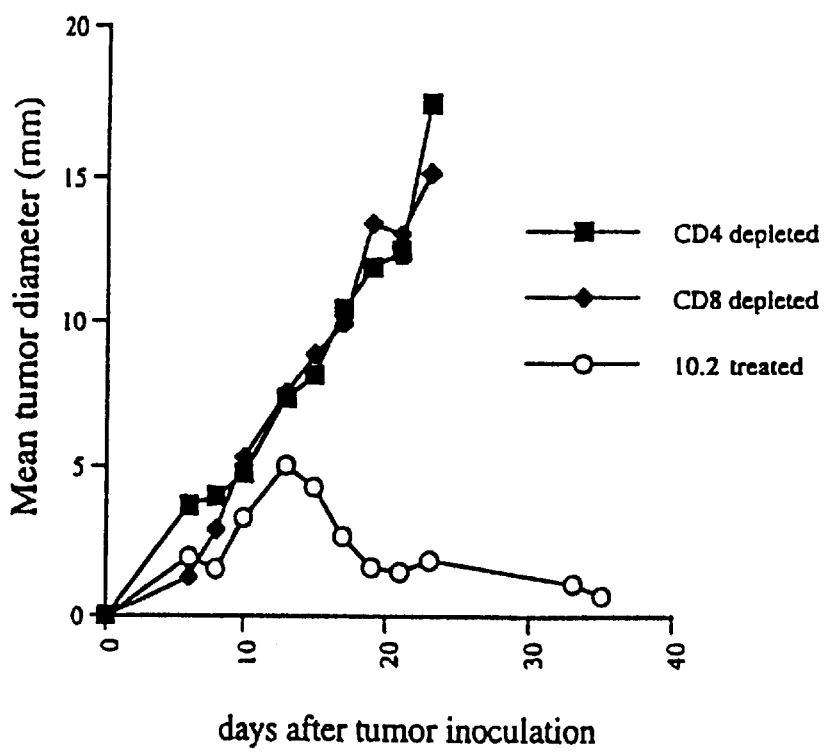
FIG. 10 is a graph depicting the effect of CD4 and CD8 depletion in 1D8-induced rejection of P815 tumor cells.

The data depicted in FIG. 10 demonstrate that depletion of either CD4 or CD8 positive T cells from mice given the P815 tumor and the 1D8 mAb are unable to reject the tumor. Without being limited to any one theory, these results suggest that both CD4 and CD8 cells are required for the effectiveness of mAb 1D8.

Figure 11:
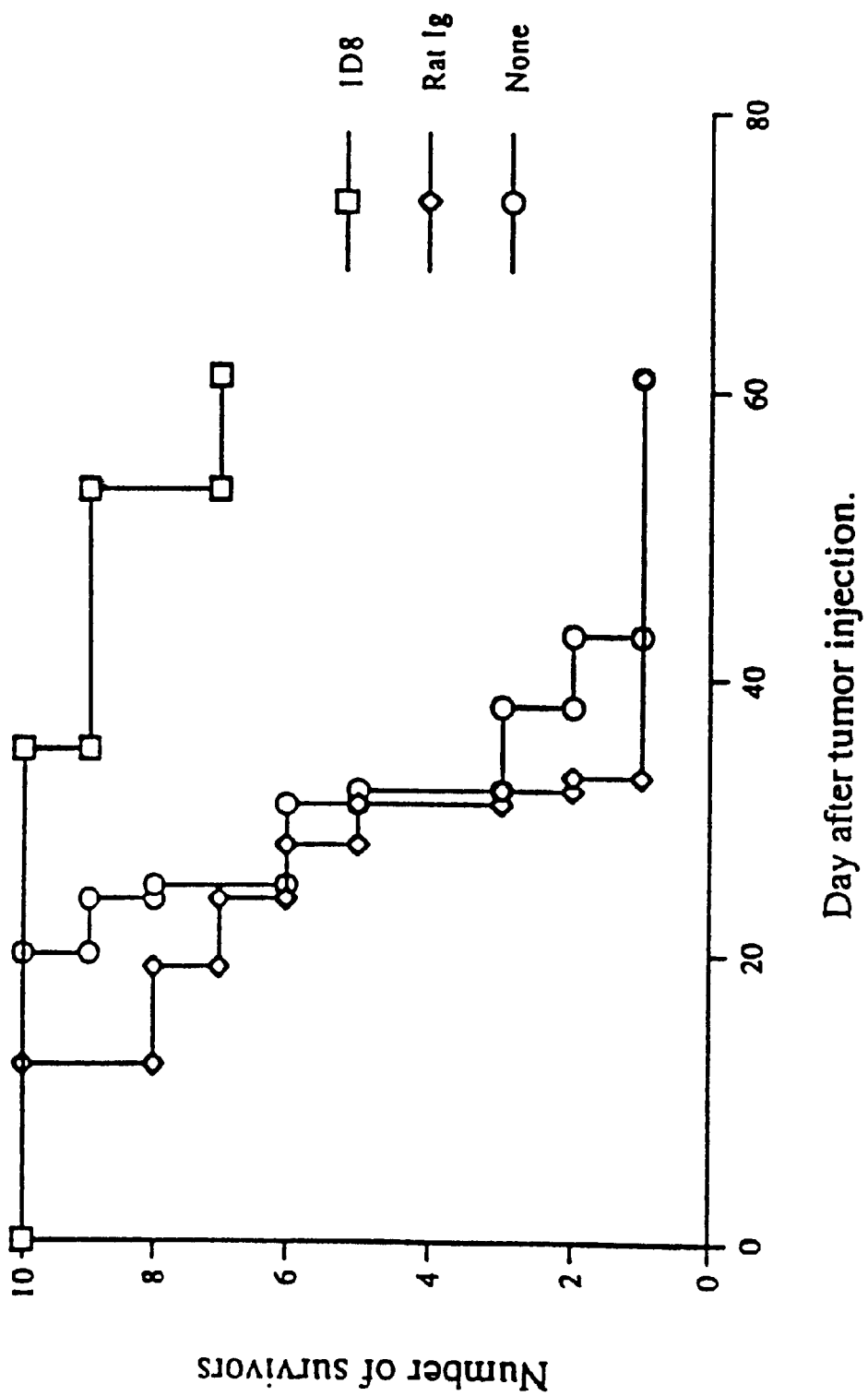
FIG. 11 is a graph depicting treatment of mice receiving intravenously injected AG104 sarcoma cells.
Figure 12A:
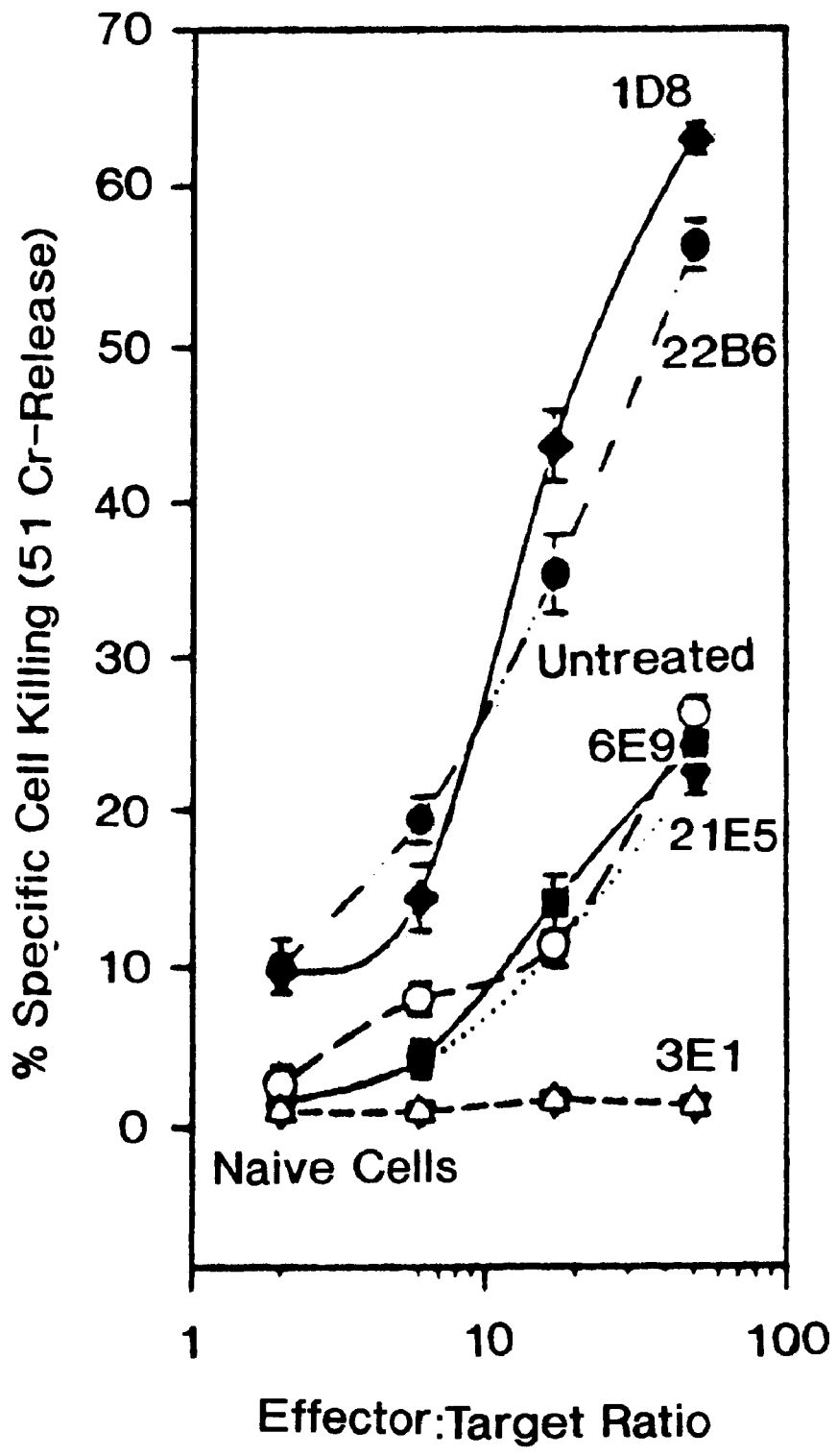
FIG. 12 (A-C) depicts (A) inhibition of in vivo generation of CTC responses during GvHD; (B) acceleration of CTC mediated killing of $BDF_1$ splenocytes by anti-4-1BB mAbs; and (C) increase in percentage of $CD8^+$ T cells in mice undergoing GvHD.
Figure 12B:
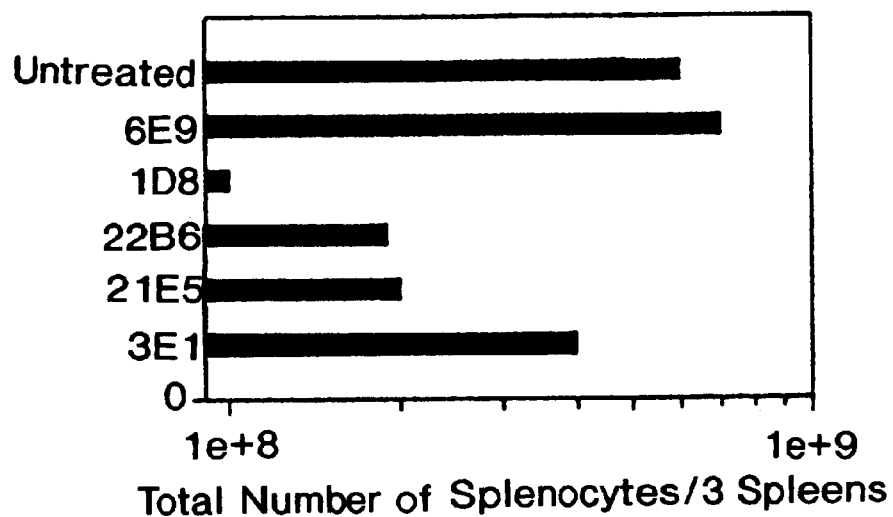
Figure 12C:
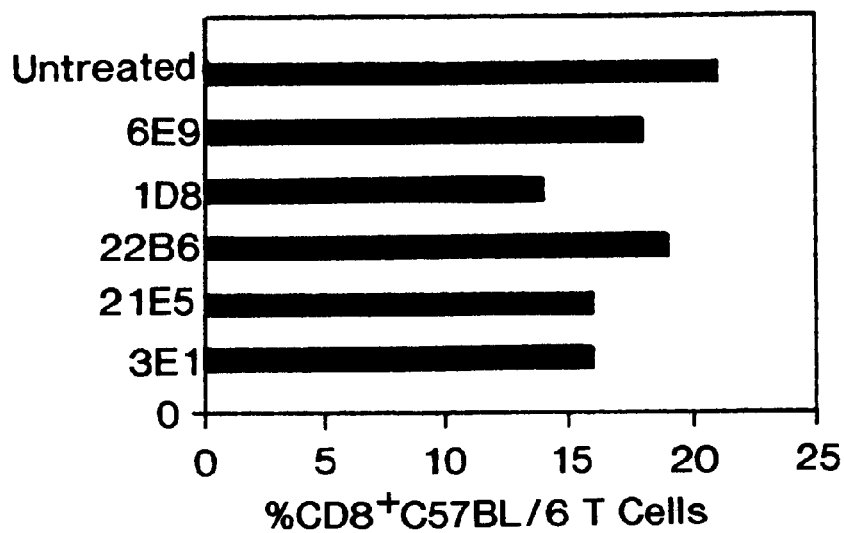

The data depicted in FIG. 11 demonstrate that the non-immunogenic sarcoma AG104 can be killed by CTL induced through 1D8 mAb stimulation. In this experiment groups of 10 Balb/C mice were injected subcutaneously with $10^5$ AG104 tumor cells. Monoclonal antibodies were injected subcutaneously on days 3 and 6 as described above. At day 60 70% of the mice survived. This result is remarkable as this tumor model is so aggressive.

X. Killing of Activated Murine T Cells

Figure 13:
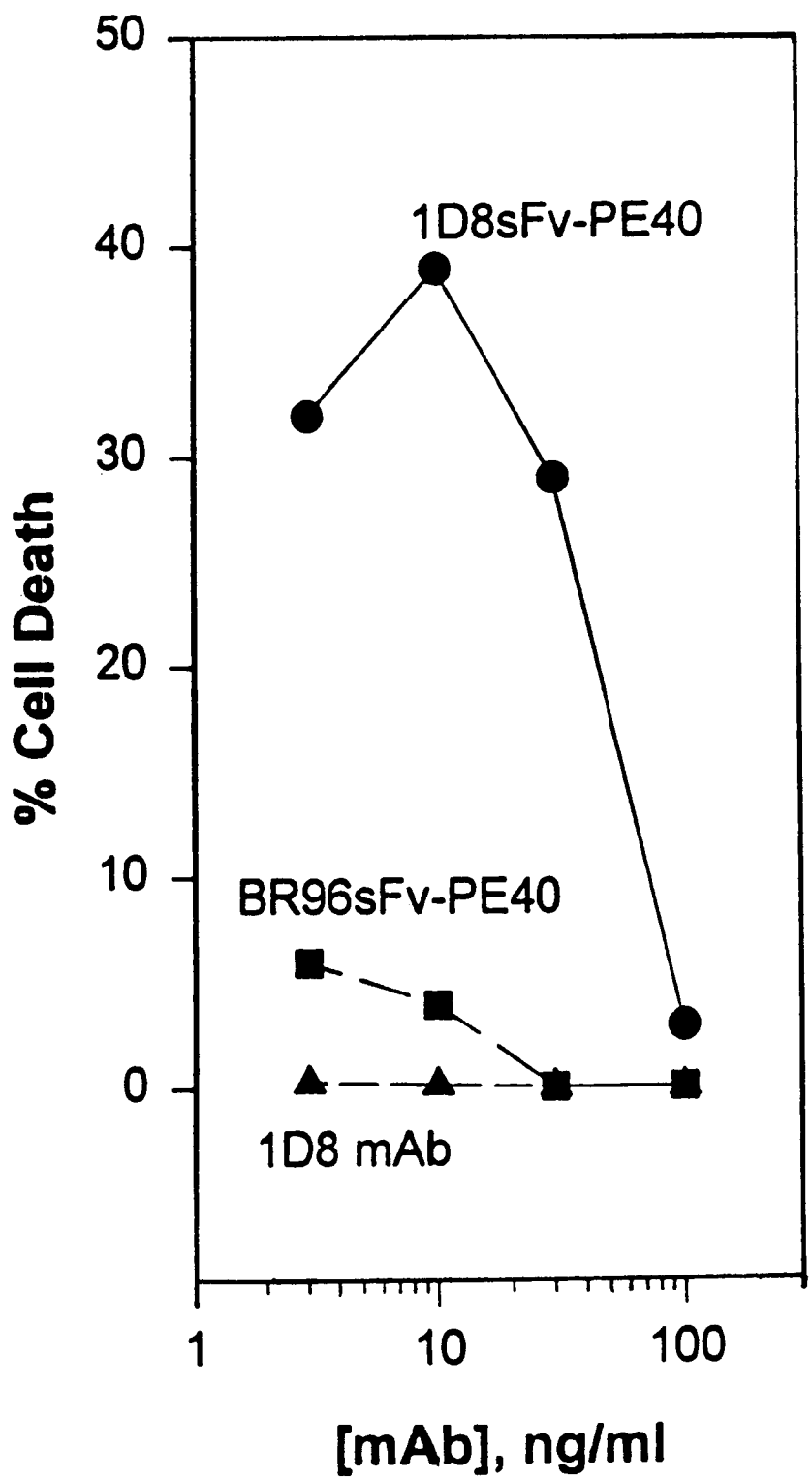
FIG. 13 is a graph depicting the killing of activated murine T cells by the anti-4-1BB-PE40 immunotoxin.

In this experiment and anti-4-1BB-PE40 immunotoxin was generated by cloning the variable regions of the 1D8 mAb from which a single chain $F_V$ was constructed. This $SF_V$ was then used to generate an $SF_V$-PE40 (Siegall et al., *Drug Dev. Res.*, 34:210–219 (1995)) immunotoxin. This immunotoxin was shown by FACS analysis to bind only to 4-1BB⁺ activated cells. The results in FIG. 13 demonstrated that this immunotoxin specifically kills activated 4-1BB⁺ T cells in a dose-dependent manner whereas a control immunotoxin does not.

XI. Blocking Development of EAE

The following experiment utilizes a murine mouse model of T cell autoimmunity, i.e., the development of experimental autoimmune (or allergic) encephalomyelitis (EAE) (see, for example, Alvord, G.C. Jr., ed. Experimental Allergic Encephalomyelitis: A Useful Model for Multiple Sclerosis, Liss, N.Y. (1984).

PL X SJL/F₁ female mice were injected intradermally with 100 µl rabbit brain myelin basic protein at 1 mg/ml in complete Freund's adjuvant on Day 0. 200 µl of a 1 µg/ml solution (PBS) of pertussis toxin was injected i.v.

Mice in groups of eight were injected i.v. on days 0, 2, and 4 with 200 µg of a 1 mg/ml PBS solution containing one of the following monoclonal antibodies (all of rat origin and being of the IgG₂A isotype) : (a) control mAb 6E9 (a rat anti-human gp39 mAb); (b) anti-4-1BB mAb 3E1; (c) anti-4-1BB mAb 3H3. Mice were analyzed for the onset of EAE by noting tail paralysis followed by hind leg paralysis (at which point animals were sacrificed for humane reasons).

Figure 14:
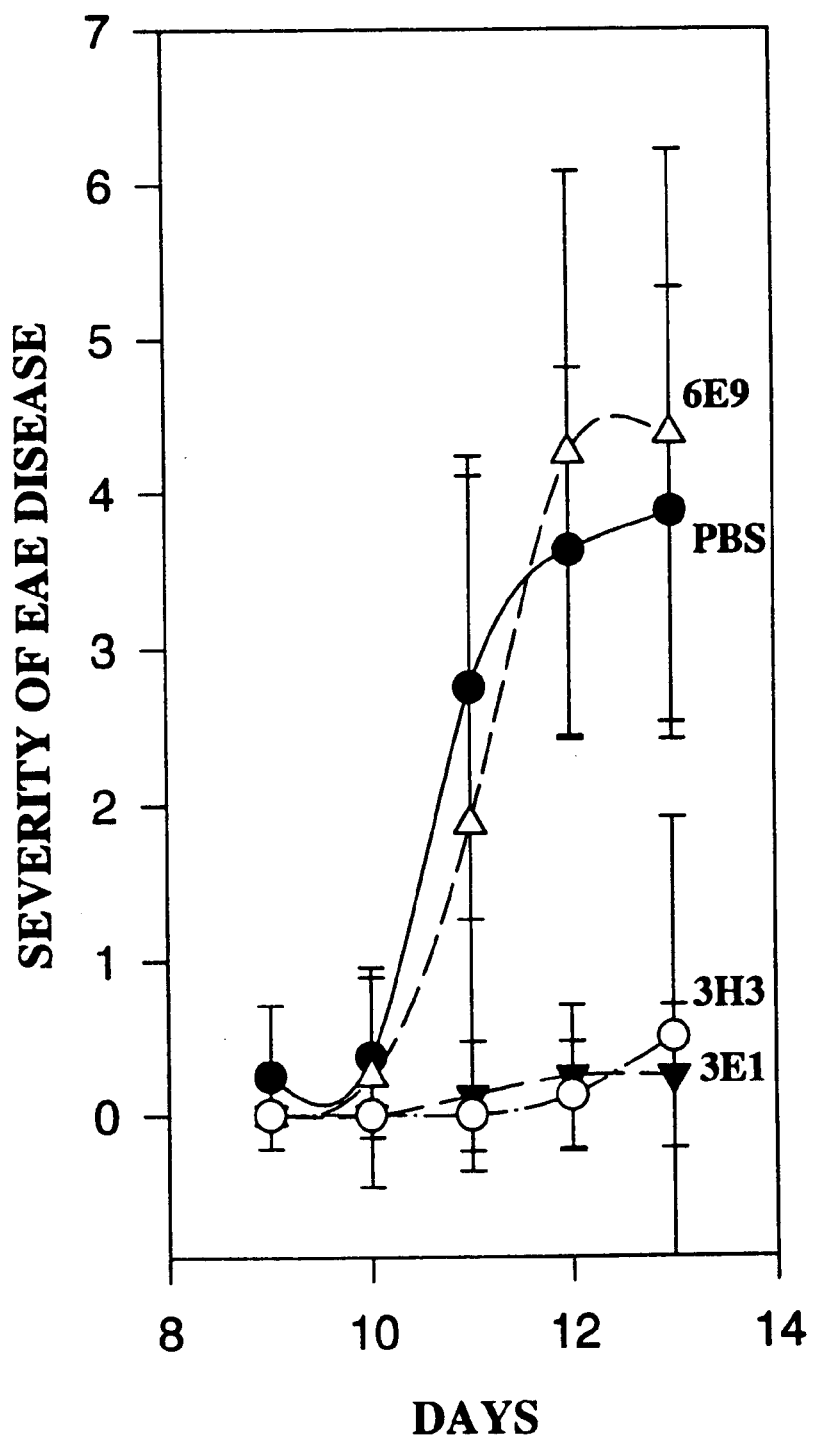
FIG. 14 is a graph depicting the ability of anti-4-1BB antibodies to block the development of experimental autoimmune encephalomyelitis.

The ability of the anti-4-1BB antibodies to block the development of EAE are demonstrated by the data depicted in FIG. 14.

Although the foregoing invention has been described in some detail by way of illustration and example for purposes of clarity of understanding, it will be obvious that certain changes and modifications may be practiced within the scope of the appended claims.

All references cited herein are incorporated by reference in their entirety for all purposes.

---

---

What is claimed is:

1. A method for potentiation of development of cytotoxic T cells in a host comprising administering to the host an effective dose of an anti-4-1BB antibody which specifically binds to the membrane proximal region of the extracellular domain of 4-1BB not involved in the binding of 4-1BB ligand to 4-1BB.

2. The method of claim 1, wherein the cytotoxic T cells kill weakly and non-immunogenic tumor cells.

3. The method of claim 2, wherein the tumor cells are mastocytoma cells or sarcoma cells.

4. The method of claim 2, wherein the anti-4-1BB antibody is monoclonal.

5. The method of claim 2, wherein the anti-4-1BB antibody is substantially human.

6. The method of claim 2, wherein the anti-4-1BB antibody is a single chain binding polypeptide comprising antigen binding regions or complementarity determining regions which specifically bind to the region of the extracellular domain of 4-1BB not involved in the binding of 4-1BB ligand to 4-1BB.

7. The method of claim 1, further comprising administering a pharmaceutically acceptable adjuvant in combination with the anti-4-1BB antibody.

8. The method of claim 1, further comprising administering a carrier in combination with the anti-4-1BB antibody.

9. The method of claim 1, further comprising administering the anti-4-1BB antibody intravenously, intraarterially, intramuscularly or subcutaneously.

\* \* \* \* \*